United States Patent
Wu et al.

(10) Patent No.: US 6,951,955 B2
(45) Date of Patent: Oct. 4, 2005

(54) PROCESS FOR THE SYNTHESIS OF INTERMEDIATES USEFUL FOR THE SYNTHESIS OF TUBULIN INHIBITORS

(75) Inventors: Yanzhong Wu, Bronx, NY (US); Sreenivasulu Megati, New City, NY (US); Constantine Gletsos, Pomona, NY (US); John Thomas Kendall, Wellesley, MA (US); Bogdan Kazimierz Wilk, New City, NY (US); Thurairajah Padmanathan, Piscataway, NJ (US); Panolil Raveendranath, Monroe, NY (US)

(73) Assignee: Wyeth Holdings Corporation, Madison, NJ (US)

(*) Notice: Subject to any disclaimer, the term of this patent is extended or adjusted under 35 U.S.C. 154(b) by 132 days.

(21) Appl. No.: 10/664,724

(22) Filed: Sep. 18, 2003

(65) Prior Publication Data

US 2004/0063904 A1 Apr. 1, 2004

Related U.S. Application Data

(60) Provisional application No. 60/412,024, filed on Sep. 20, 2002.

(51) Int. Cl.[7] .............................................. C07C 205/02
(52) U.S. Cl. ...................................... 560/125; 560/126
(58) Field of Search ................................. 546/125, 126

(56) References Cited

FOREIGN PATENT DOCUMENTS

| WO | WO 96/33211 | 10/1996 |
|---|---|---|
| WO | WO 99/32509 | 8/1999 |
| WO | WO 03/072754 | 9/2003 |

OTHER PUBLICATIONS

Database–Crossfire Beilstein Online; Database–Accession No. 277319; XP002273035; English.
Ann. Chim. (Paris); vol. 8, No., 10; p. 364; 1907.
J.P. Brown, et al.; Journal of the Chemical Society; pp. 859–867; 1949.
N.M. Waldron, et al.; Journal of the Chemical Society; pp. 1914–1917; 1968.
Cecile Pascal, et al.; Journal of Organic Chemistry; vol. 63; No. 18, pp. 6414–6420; 1998.
Corey, E., et al.; Tetrahedron Letters, p. 2325, (1967).
Chakraborty, T.K., et al.; Tetrahedron Letters, 32, pp. 7597–7600 (1991).
Semko, C.M.; J. Org. Chem., 58, p. 696, (1993).
Yamamoto, H., et al; Synlett, p. 721 (1995).
Davis, et al.; J. Org. Chem., 61, p. 440, (1996).
Davis, et al.; J. Org. Chem, 64, p. 1403 (1999).
Vedejs, E., et al.; J. Org. Chem., 2001, 66, pp. 7355–7364 (2001).

*Primary Examiner*—Taofiq Solola
(74) *Attorney, Agent, or Firm*—Joy S. Goudie

(57) ABSTRACT

The invention is a process for the preparation of compounds of the Formula I:

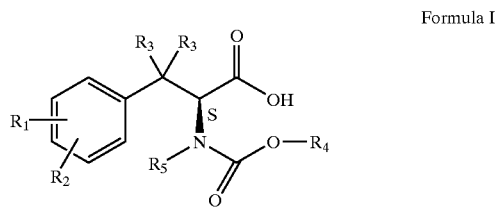

Formula I where $R_1$, $R_2$, $R_3$, $R_4$ and $R_5$ are defined in the specification, which are intermediates useful for the preparation of tubulin inhibitors which are useful in the treatment of cancer.

45 Claims, No Drawings

PROCESS FOR THE SYNTHESIS OF INTERMEDIATES USEFUL FOR THE SYNTHESIS OF TUBULIN INHIBITORS

"This application claims priority from copending provisional Application No. 60/412,024 filed Sep. 20, 2002 the entire disclosure of which is hereby incorporated by reference."

FIELD OF THE INVENTION

This invention relates to a novel process for the preparation of racemic and asymmetric intermediates useful for the preparation of tubulin inhibitors which are useful in the treatment of cancer.

BACKGROUND OF THE INVENTION

Hemiasterlin analogs 1 with substituents as reported (WO 9932509) are synthesized by coupling carboxylic acid 2, with intermediate amine 3.

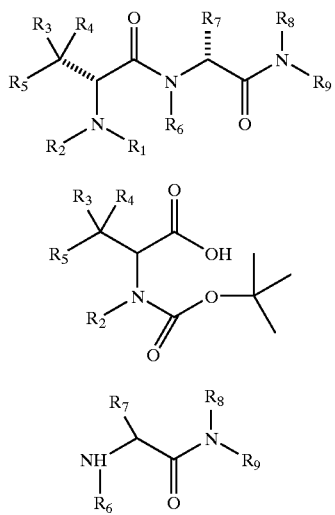

The asymmetric synthesis of N-(tert-butoxycarbonyl)-N, β,β-trimethyl-L-phenylalanine from 3-methyl-3-phenylbutanoic acid using a chiral oxazolidine route is described (WO 9932509). In particular, this route is limited to small scale synthesis because trisyl azide as a reagent is a safety hazard and the azide intermediate produced therefrom makes this route not suitable for scale-up. Still further, purification in several of the steps requires chromatography and additionally, some racemization in the last synthetic step, makes this route less desirable for the scale-up.

Reported also is the preparation of N,N-di(tert-butoxycarbonyl)-(2S)-2-[(benzothiazole-2-sulfonyl)methylamino]-3-methyl-(1-methylindol-3-yl)butyramide (4, Vedejs, E et. al J. Org. Chem, 2001, 66, 7355–7364) using asymmetric Strecker methodology (Chakraborty, T. K. et. al, Tetrahedron Letters, 1991, 32, 7597–7600). However, the described synthetic methodology cannot be used effectively for scaleup in the synthesis of acid 2 because of the use of tributyltin cyanide and the necessary purification of intermediates by column chromatography.

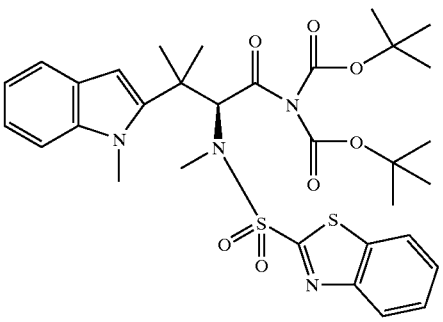

Thus, there is need in the art for a process to prepare carboxylic acid 2 which overcomes azide intermediates and also overcomes the need for purification by column chromatography.

Further, there is a need for a synthesis of carboxylic acid 2, in particular (S), which is used in the preparation of hemiasterlin analogs 1.

In particular, there is a need for a process to prepare (S) acid 2 used to prepare N,β,β-trimethylphenylalanyl-N¹-[(1S,2E)-3-carboxy-1-isopropylbut-2-enyl]-N¹,3-dimethyl-L-valinamide a tubulin inhibitor useful in the treatment of cancer.

BRIEF SUMMARY OF THE INVENTION

The present invention provides a process for the preparation of a compound of Formula I:

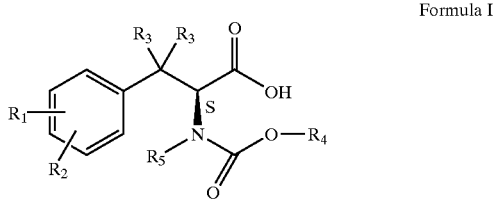

Formula I wherein:

$R_1$ and $R_2$ are independently selected from H, straight chain alkyl of 1 to 4 carbon atoms, halogen and alkoxy of 1 to 4 carbon atoms;

$R_3$ is straight chain alkyl of 1 to 4 carbon atoms;

$R_4$ is straight chain alkyl of 1 to 4 carbon atoms and branched chain alkyl of 3 to 4 carbon atoms;

$R_5$ is straight chain alkyl of 1 to 4 carbon atoms;

comprising:

a) treating a nitrile of the formula:

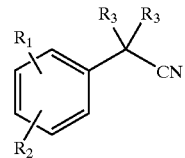

with a reducing agent followed by acid hydrolysis to obtain an aldehyde of the formula:

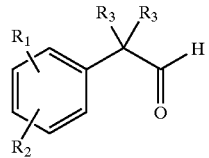

b) reacting the aldehyde (step a) with alkali metal cyanide in the presence of an alkylamine of the formula $R_5NH_2$ to obtain a nitrile of the formula:

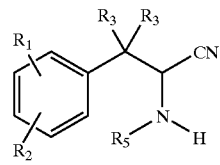

c) hydrolyzing the nitrile (step b) with an alkali metal hydroxide to give an amide of the formula:

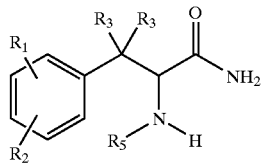

d) reacting the amide (step c) with an organic carbonate of the formula $O[CO_2R_4]_2$ to give optionally isolated blocked amine of the formula:

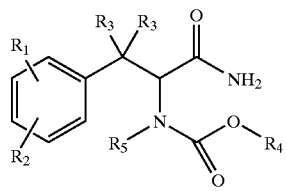

e) reacting optionally isolated blocked amine (step d) with an organic carbonate of the formula $O[CO_2R_4]_2$ wherein each $R_4$ is taken independently in the presence of dimethylaminopyridine(DMAP) to obtain a triblocked amide of the formula:

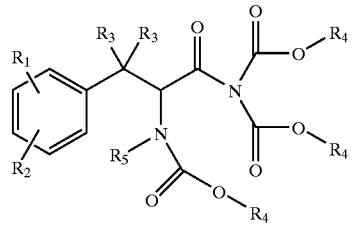

f) hydrolyzing triblocked amide (step e) with an alkali metal base to give racemic blocked amine of the formula:

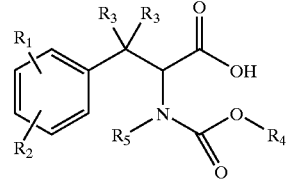

g) reacting racemic blocked amine (step f) with a resolving base ($NH_2$-resolving base) to obtain a resolved blocked amine salt of the formula:

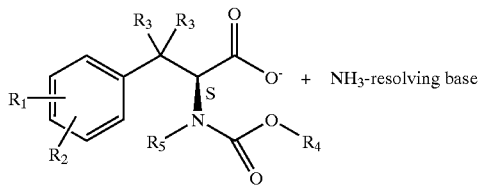

h) treating the resolved blocked amine salt (step g) with an aqueous alkali metal hydroxide and acidifying with acid to give a compound Formula I:

Formula I

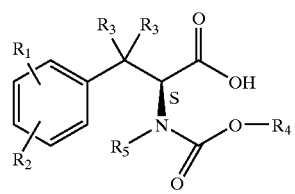

An additional embodiment of the present invention provides a process for the preparation of a compound of Formula I:

Formula I

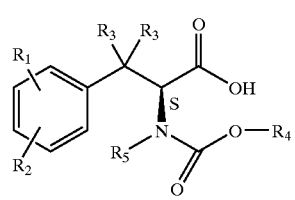

wherein:

$R_1$ and $R_2$ are independently selected from H, straight chain alkyl of 1 to 4 carbon atoms, halogen and alkoxy of 1 to 4 carbon atoms;

$R_3$ is straight chain alkyl of 1 to 4 carbon atoms;

$R_4$ is straight chain alkyl of 1 to 4 carbon atoms and branched chain alkyl of 3 to 4 carbon atoms;

$R_5$ is straight chain alkyl of 1 to 4 carbon atoms;

comprising:

a) treating a nitrile of the formula:

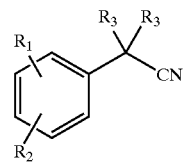

with a reducing agent followed by acid hydrolysis to obtain an aldehyde of the formula;

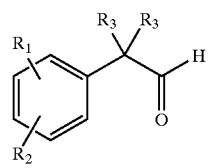

b) reacting the aldehyde (step a) with alkali metal cyanide in the presence of an alkyl amine of the formula $R_5NH_2$ to obtain nitrile of the formula:

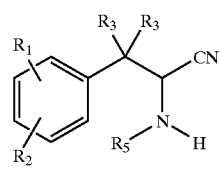

c) hydrolyzing the nitrile (step b) with an alkali metal hydroxide to give an amide of the formula:

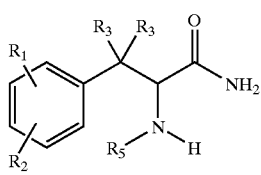

d) reacting the amide (step c) with an organic carbonate, of the formula $O[CO_2R_4]_2$ in the presence of dimethylaminopyridine (DMAP) to obtain a triblocked amide of the formula:

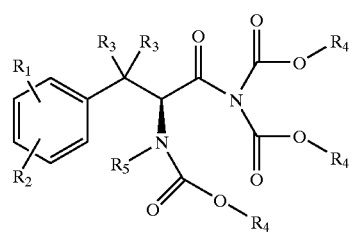

e) hydrolyzing triblocked amide (step d) with an alkali metal hydroxide to give racemic blocked amine of the formula:

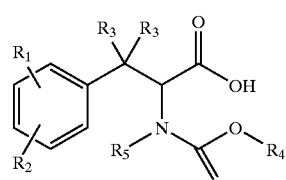

f) reacting racemic blocked amine (step e) with a resolving base ($NH_2$-resolving base) to obtain a resolved blocked amine salt of the formula:

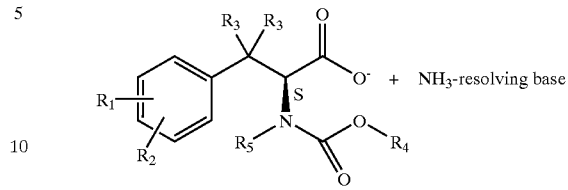

and g) treating the resolved blocked amine salt with aqueous alkali metal hydroxide and acidifying with acid to give a compound of Formula I:

Formula I

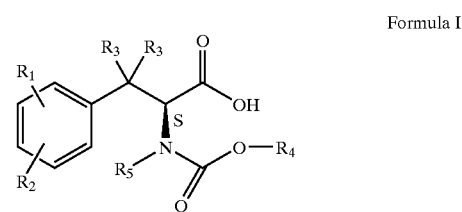

An additional embodiment of the present invention provides a process for the preparation of a compound of the formula:

Formula I

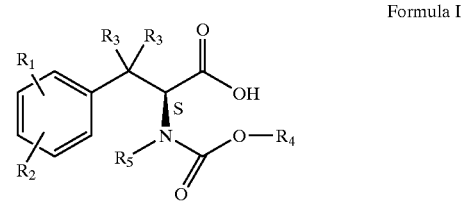

wherein:

$R_1$ and $R_2$ are independently selected from H, straight chain alkyl of 1 to 4 carbon atoms, halogen and alkoxy of 1 to 4 carbon atoms;

$R_3$ is straight chain alkyl of 1 to 4 carbon atoms;

$R_4$ is straight chain alkyl of 1 to 4 carbon atoms and branched chain alkyl of 3 to 4 carbon atoms;

$R_5$ is straight chain alkyl of 1 to 4 carbon atoms;

comprising:

a) reacting a racemic blocked amine of the formula

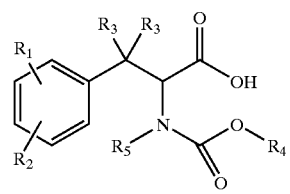

with a resolving base (NH$_2$-resolving base) to obtain a resolved blocked amine salt of the formula:

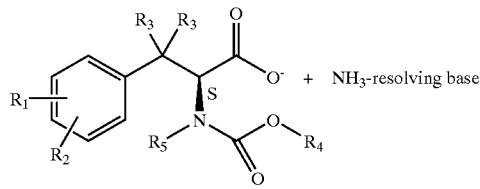

and b) treating the resolved blocked amine salt with aqueous alkali metal hydroxide and acidifying with acid to give a compound of Formula I:

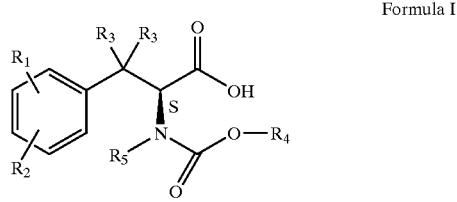

Formula I

A further embodiment of the present invention provides a process for the preparation of a compound of Formula I:

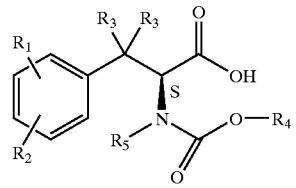

wherein:
R$_1$ and R$_2$ are independently selected from H, straight chain alkyl of 1 to 4 carbon atoms, halogen and alkoxy of 1 to 4 carbon atoms;
R$_3$ is straight chain alkyl of 1 to 4 carbon atoms;
R$_4$ is straight chain alkyl of 1 to 4 carbon atoms and branched chain alkyl of 3 to 4 carbon atoms;
R$_5$ is straight chain alkyl of 1 to 4 carbon atoms;
comprising:
a) deblocking substituted amine of the formula:

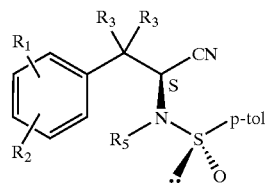

with acid to give nitrile of the formula:

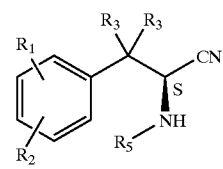

b) hydrolyzing the nitrile (step a) in the presence of an alkali metal hydroxide to obtain amide of the formula:

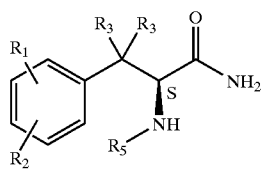

c) reacting the amide (step b) with an organic carbonate of the formula O[CO$_2$R$_4$]$_2$ to obtain blocked amine of the formula:

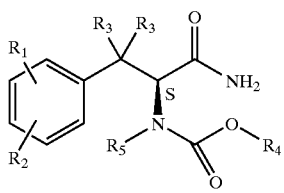

optionally isolated and further reacted with an organic carbonate of the formula O[CO$_2$R$_4$]$_2$ wherein each R$_4$ is taken independently in the presence of dimethylaminopyridine (DMAP) to give a triblocked amide of the formula:

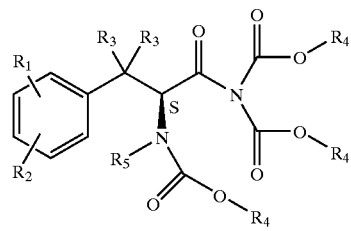

and d) hydrolyzing triblocked amide (step c) with an alkali metal hydroxide and acidifying with acid to obtain a compound of Formula I:

Formula I

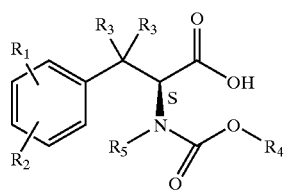

A further embodiment of the present invention provides a process for the preparation of a compound of Formula I:

Formula I

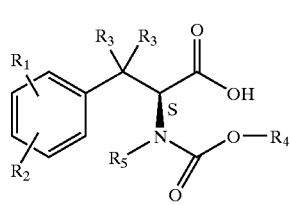

wherein:
R$_1$ and R$_2$ are independently selected from H, straight chain alkyl of 1 to 4 carbon atoms, halogen and alkoxy of 1 to 4 carbon atoms;
R$_3$ is straight chain alkyl of 1 to 4 carbon atoms;
R$_4$ is straight chain alkyl of 1 to 4 carbon atoms and branched chain alkyl of 3 to 4 carbon atoms;
R$_5$ is straight chain alkyl of 1 to 4 carbon atoms;
comprising:
a) deblocking substituted amine of the formula:

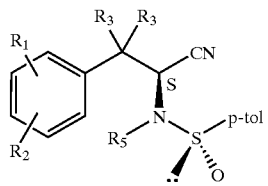

with acid to give nitrile of the formula;

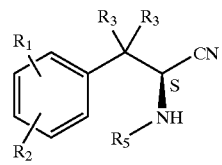

b) hydrolyzing the nitrile (step a) in the presence of an alkali metal hydroxide to obtain an amide of the formula:

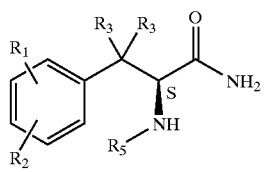

c) reacting the amide (step b) with an organic carbonate of the formula O[CO$_2$R$_4$]$_2$ in the presence of dimethylaminopyridine (DMAP) to give triblocked amide of the formula:

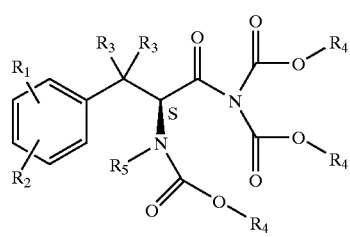

and;
d) hydrolyzing triblocked amide (step c) with an alkali metal hydroxide and acidifying with acid to obtain a compound of Formula I:

Formula I

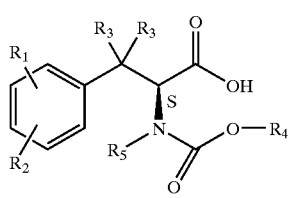

A further embodiment of the invention provides a process for the preparation of an aldehyde of the formula:

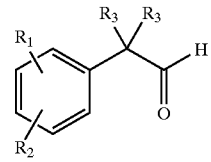

wherein:
R$_1$ and R$_2$ are independently selected from H, straight chain alkyl of 1 to 4 carbon atoms, halogen and alkoxy of 1 to 4 carbon atoms;
R$_3$ is straight chain alkyl of 1 to 4 carbon atoms;
comprising rearrangement of substituted oxirane of the formula:

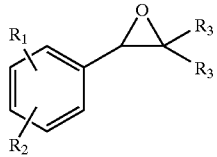

with tris(pentafluorophenyl) borane to afford an aldehyde of the formula:

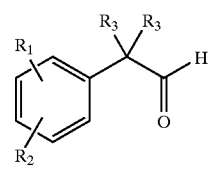

An additional embodiment of the invention provides a process for the preparation of a carboxylic acid of the formula:

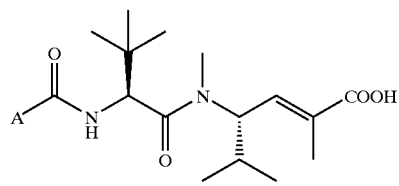

wherein:
A is selected from the group

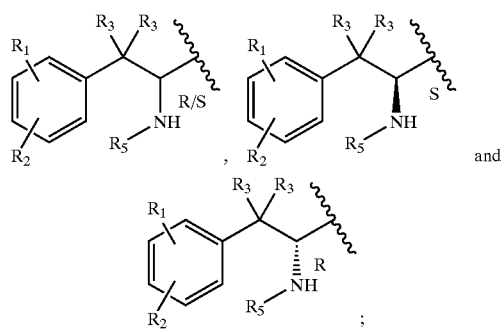

R$_1$ and R$_2$ are independently selected from H, straight chain alkyl of 1 to 4 carbon atoms, halogen and alkoxy of 1 to 4 carbon atoms;

$R_3$ is straight chain alkyl of 1 to 4 carbon atoms;
$R_5$ is straight chain alkyl of 1 to 4 carbon atoms;
comprising:
a) coupling an amino acid of the formula selected from the group:

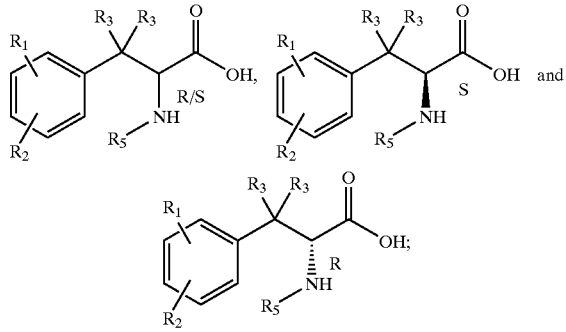

with an ester of the formula:

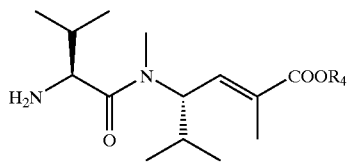

$R_4$ is straight chain alkyl of 1 to 4 carbon atoms and branched chain alkyl of 3 to 4 carbon atoms;
in the presence of a coupling agent and an organic base to obtain an ester of the formula:

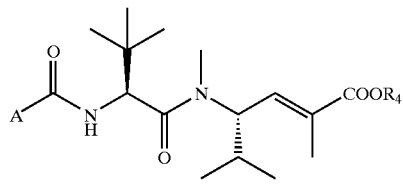

b) hydrolyzing the ester of step a) with an alkali metal hydroxide and acidifying with acid affords a carboxylic acid of the formula:

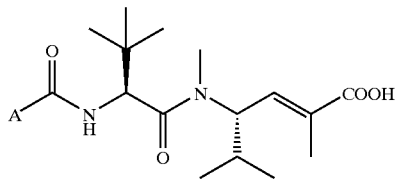

An additional embodiment of the invention provides a process for the preparation of a carboxylic acid of the formula:

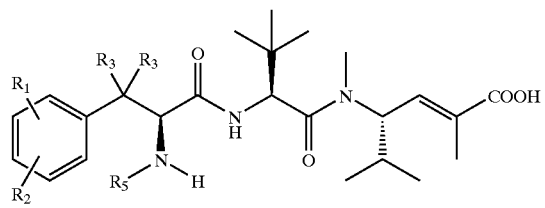

wherein:
$R_1$ and $R_2$ are independently selected from H, straight chain alkyl of 1 to 4 carbon atoms, halogen and alkoxy of 1 to 4 carbon atoms;

$R_3$ is straight chain alkyl of 1 to 4 carbon atoms;
$R_5$ is straight chain alkyl of 1 to 3 carbon atoms;
comprising:
a) coupling an amino acid of the formula:

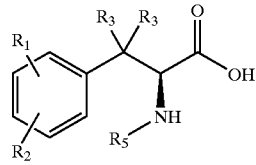

with an ester of the formula:

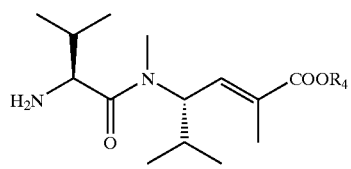

$R_4$ is straight chain alkyl of 1 to 4 carbon atoms and branched chain alkyl of 3 to 4 carbon atoms;
in the presence of a coupling agent and an organic base to obtain an ester of the formula:

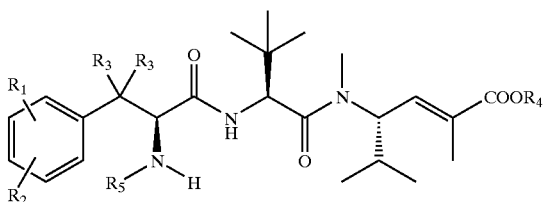

b) hydrolyzing the ester of step a) with an alkali metal hydroxide and acidifying with acid to obtain a carboxylic acid of the formula:

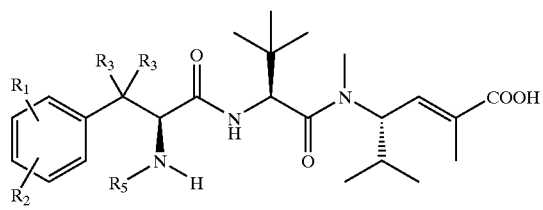

An additional embodiment of the invention provides a process for the preparation of a carboxylic acid of the formula:

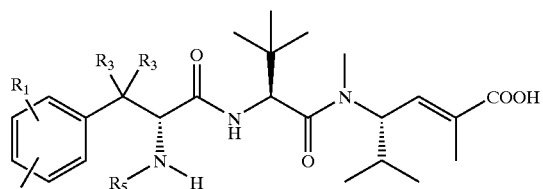

wherein:
$R_1$ and $R_2$ are independently selected from H, straight chain alkyl of 1 to 4 carbon atoms, halogen and alkoxy of 1 to 4 carbon atoms;
$R_3$ is straight chain alkyl of 1 to 4 carbon atoms;

$R_5$ is straight chain alkyl of 1 to 3 carbon atoms;
comprising:
a) coupling an amino acid of the formula:

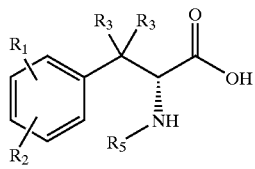

with an ester of the formula:

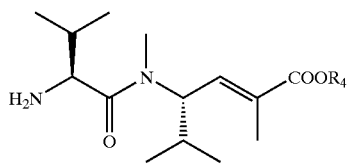

$R_4$ is straight chain alkyl of 1 to 4 carbon atoms and branched chain alkyl of 3 to 4 carbon atoms;
in the presence of a coupling agent and an organic base to obtain an ester of the formula:

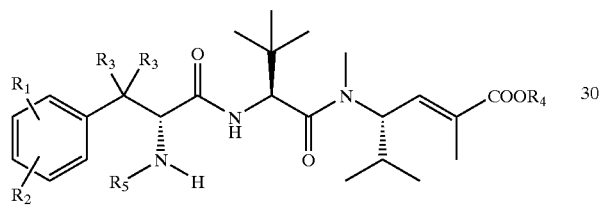

b) hydrolyzing the ester of step a) with an alkali metal hydroxide and acidifying with acid to obtain a carboxylic acid of the formula:

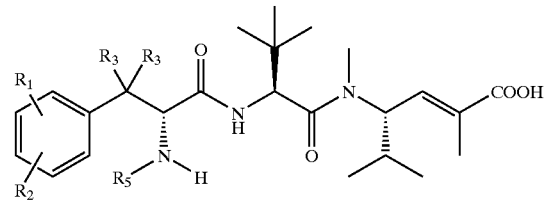

A further embodiment of the invention provides a process for the preparation of an aldehyde of the formula:

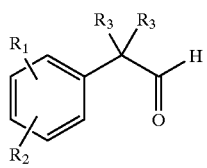

wherein:
$R_1$ and $R_2$ are independently selected from H, straight chain alkyl of 1 to 4 carbon atoms, halogen and alkoxy of 1 to 4 carbon atoms;
$R_3$ is straight chain alkyl of 1 to 4 carbon atoms;
$R_4$ is straight chain alkyl of 1 to 4 carbon atoms and branched chain alkyl of 3 to 4 carbon atoms;
$R_5$ is straight chain alkyl of 1 to 4 carbon atoms;
comprising:
a) alkylating benzylnitrile of the formula:

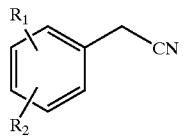

with an alkylating agent $R_3LG$, in the presence of a strong base, to obtain a nitrile of the formula:

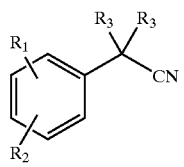

and
b) reducing a nitrile of step a with a reducing agent to give an aldehyde of the formula:

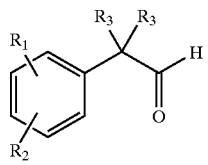

An additional embodiment of the present invention provides a process for the preparation of a compound of the formula:

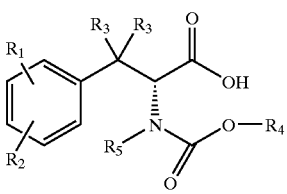

wherein:
$R_1$ and $R_2$ are independently selected from H, straight chain alkyl of 1 to 4 carbon atoms, halogen and alkoxy of 1 to 4 carbon atoms;
$R_3$ is straight chain alkyl of 1 to 4 carbon atoms;
$R_4$ is straight chain alkyl of 1 to 4 carbon atoms and branched chain alkyl of 3 to 4 carbon atoms;
$R_5$ is straight chain alkyl of 1 to 4 carbon atoms;
comprising:
a) reacting a racemic blocked amine of the formula

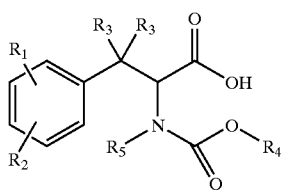

with a resolving base (NH$_2$-resolving base) to obtain a resolved blocked amine salt of the formula:

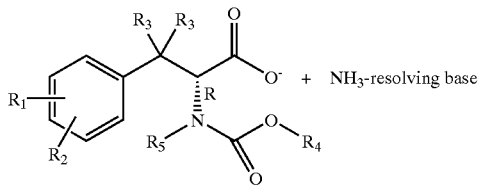

and b) treating the resolved blocked amine salt with aqueous alkali metal hydroxide and acidifying with acid to give a compound of the Formula

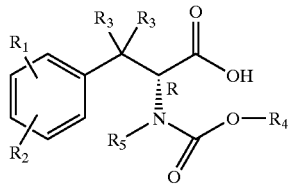

The present invention provides the following compounds:
3-methyl-2-(methylamino)-3-phenylbutanenitrile,
N,β,β-trimethylphenylalaninamide,
N,β,β-trimethylphenylalanine,
N-(tert-butoxycarbonyl)-N,β,β-trimethylphenylalaninamide,
N,N,N-tris(tert-butoxycarbonyl)-N,β,β-trimethylphenylalaninamide,
N-(tert-butoxycarbonyl)-N,β,β-trimethylphenylalanine,
(S)—N-(2-methyl-2-phenyl-propylidene)-p-toluenesulfinamide
(S$_S$,2S)—N-(p-toluenesulfinyl)-2-amino-3-methyl-3-phenylbutyronitrile and
S$_S$,2R)—N-(p-toluenesulfinyl)-2-amino-3-methyl-3-phenylbutyronitrile,
(S$_S$,2S)—N-(p-toluenesulfinamido-methyl)-3-methyl-3-phenylbutanenitrile,
(2S)-3-methyl-2-(methylamino)-3-phenylbutanenitrile,
N,β,β-trimethyl-L-phenylalaninamide,
N-(tert-butoxycarbonyl)-N,β,β-trimethyl-L-phenylalaninamide,
N,N,N-tris(tert-butoxycarbonyl)-N,β,β-trimethyl-L-phenylalaninamide,
salt of N-(tert-butoxycarbonyl)-N,β,β-trimethyl-L-phenylalanine with (S)-(–)-α-methylbenzylamine (SAMBA) and
salt of N-(tert-butoxycarbonyl)-N,β,β-trimethyl-D-phenylalanine with (R)-(+)-α-methylbenzylamine (RAMBA).

The following experimental details are set forth to aid in an understanding of the invention, and are not intended, and should not be construed to limit in any way the invention set forth in the claims that follow thereafter.

DETAILED DESCRIPTION OF THE INVENTION

Terms and Definitions

Halogen, as used herein means fluoro, chloro, bromo and iodo.

Alkyl as used herein means a straight chain having from 1 to 4 carbon atoms. Exemplary alkyl groups include methyl, ethyl, propyl, and butyl.

Straight chain alkyl as used herein means a straight chain having from 1 to 4 carbon atoms. Exemplary alkyl groups include methyl, ethyl, propyl, and butyl.

Branched chain alkyl as used herein means a branched chain having 3 or 4 carbon atoms. Exemplary branched alkyl groups include isopropyl and tertiary butyl.

Alkoxy as used herein means an alkyl-O— group in which the alkyl group is as previously described. Exemplary alkoxy groups include but are not limited to methoxy, ethoxy, n-propoxy, and n-butoxy.

A strong base as used herein means a tert-butoxyalkali metal base. Additional strong bases include sodium hydride, potassium hydride, sodium hydroxide, and lithium diisopropylamide. Preferred strong bases include potassium tert-butoxide ($^t$BuOK), sodium tert-butoxide ($^t$BuONa), or lithium tert-butoxide ($^t$BuOLi), most preferably potassium tert-butoxide ($^t$BuOK).

Alkali metal cyanide as used herein means an alkali metal cyanide salt. Preferred are sodium cyanide, potassium cyanide and lithium cyanide, most preferably potassium cyanide.

Alkali metal hydroxide, preferably, means sodium hydroxide, potassium hydroxide and lithium hydroxide, most preferably lithium hydroxide.

Reducing agent as used herein means an agent which adds hydride and includes tin chloride/hydrochloric acid, lithium aluminum hydride and diisobutylaluminum hydride (DIBAL-H).

Oxidizing agent as used herein means an agent which has an O—O bonding such as hydrogen peroxide.

Organic carbonate as used herein means a compound of the formula O[CO$_2$R$_4$]$_2$ where R$_4$ is alkyl as previously defined. Preferred is t-butyl dicarbonate when t means tert.

Organic base as used herein means an alkylamine base which includes triethylamine, N,N-diethylmethylamine, N,N-diethylaniline, N,N-diethylethylenediamine, or N,N-diisopropylethylamine. Further organic bases include dimethylaminopyridine(DMAP) with diisopropylethylamine (DIEA), N-methylmorpholine, N-methylpyrrolidine, 2,6-di-tertbutyl-4-methylpyridine or pyridine.

A resolving base as used herein means a chiral amine (R or S) capable of forming a pair of salts (R and S) with a racemic carboxylic acid. The pair of salts are capable of being separated one from the other by crystallization or high pressure liquid chromatography. Exemplary resolving bases include (S)-(–)-α-methylbenzylamine, (S)-(–)-α-methyl-4-nitro-benzylamine, (1R,2S)-(–)-norephedrin, (1S,2R)-(+)-norephedrin and (R)-(+)-α-methylbenzylamine.

The synthesis of compounds of Formula I is illustrated in Schemes 1 and 2. As shown in Scheme 1, benzylnitrile 5 which is either commercially available or can be easily made from known and readily available reagents, where R$_1$ and R$_2$ are hereinbefore defined is dialkylated with R$_3$LG in the presence of a strong base. Preferred strong bases include potassium tert-butoxide ($^t$BuOK), sodium tert-butoxide ($^t$BuONa), or lithium tert-butoxide ($^t$BuOLi), most preferably potassium tert-butoxide ($^t$BuOK), and an alkylating agent R$_3$LG where R$_3$ is hereinbefore defined and LG is a leaving group which includes but not limited to chloro, bromo, p-toluenesulfonyl and methanesulfonyl. Preferred alkylating agents include methyl iodide or methyl bromide, most preferably iodomethane (methyl iodide) (CH$_3$I) or alternatively methyl bromide in the presence of sodium iodide or tetrabutyl ammonium iodide in a solvent which includes tetrahydrofuran (THF), acetonitrile, N,N-dimethylformamide (DMF) or N-methylpyrrolidinone, preferably THF to afford nitrile 6 followed by reduction with a reducing agent which includes tin chloride/HCl, lithium aluminum hydride and diisobutylaluminum hydride (DIBAL-H) preferably diisobutylaluminum hydride (DIBAL-H) followed by acid hydrolysis to give aldehyde 7.

Aldehyde 7 is converted to nitrile 8 by the Strecker reaction with an alkali metal cyanide preferably potassium cyanide (KCN) or sodium cyanide (NaCN) or optionally with (dialkyl)aluminum cyanide or (trialkyl)silyl cyanide and an alkylamine ($R_5NH_2$), optionally as a salt which includes the hydrochloride or hydrobromide salt, in an aqueous alcohol which includes methanol, ethanol, propanol and 2-propanol, preferably aqueous methanol, in quantitative yield. Nitrile 8 is hydrolyzed to amide 9 by treating with an alkali metal hydroxide selected from the group lithium hydroxide (LiOH), sodium hydroxide and potassium hydroxide preferably lithium hydroxide optionally in the presence of an oxidizing agent such as hydrogen peroxide ($H_2O_2$). Protection of the amine group of amide 9 as well as activation of the amide for hydrolysis is accomplished by reaction with an organic carbonate of the formula $O[CO_2R_4]_2$ where $R_4$ is hereinbefore defined and each $R_4$ is taken independently in a solvent such as acetonitrile to afford blocked amine 10. Protecting with the tert-butoxycarbonyl (Boc) group is preferred. Further reaction of blocked amine 10 with an organic carbonate of the formula $O[CO_2R_4]_2$ preferably di-tert-butyl dicarbonate in the presence of dimethylaminopyridine(DMAP) (at about 10% mol. Percent) optionally in the presence of an additional organic base preferably diisopropylethylamine (DIEA) in a solvent such as acetonitrile gives optionally isolated triblocked amide 11. Hydrolysis of triblocked amide 11 with an alkali metal hydroxide, preferably aqueous sodium hydroxide affords racemic blocked amine 12. Racemic blocked amine 12 is reacted with a resolving base ($NH_2$-resolving base) 13 which include but are not limited to (S)-(−)-α-methylbenzylamine, (S)-(−)-α-methyl-4-nitro-benzylamine, (1R,2S)-(−)-norephedrin, and (1S,2R)-(+)-norephedrin in a solvent such as ether to obtain the resolved blocked amine salt 14. Preferably, resolving base (S)-(−)-α-methylbenzylamine (SAMBA) is reacted with N-(tert-butoxycarbonyl)-N,β,β-trimethyl-L-phenylalanine to afford the salt of N-(tert-butoxycarbonyl)-N,β,β-trimethyl-L-phenylalanine with (S)-(−)-α-methylbenzylamine (SAMBA) 14a. Resolved blocked amine salt 14 is treated with an alkali metal hydroxide, further including sodium carbonate preferably aqueous sodium hydroxide or sodium carbonate and the product as Formula I is isolated after further reaction with acid to afford compounds of Formula I. Commonly used acids include hydrochloric and sulfuric, preferably citric acid. Preferably, treatment of salt of N-(tert-butoxycarbonyl)-N,β,β-trimethyl-L-phenylalanine with (S)-(−)-(α)-methylbenzylamine (SAMBA) 14a with an alkali metal hydroxide preferably aqueous sodium hydroxide (NaOH) or sodium carbonate followed by acidifying to a pH 6 or less, preferably to a pH of 3–6, more preferably 4–6 and most preferably to 5–6 with citric acid provides N-(tert-butoxycarbonyl)-N,β,β-trimethyl-L-phenylalanine of Formula I. Optionally, using the conditions as described in Scheme I, racemic blocked amine 12 is reacted with a resolving base ($NH_2$-resolving base) 13 which includes (R)-(+)-α-methylbenzylamine to afford the (R) resolved blocked amine salt which may be treated with an alkali metal hydroxide using conditions as described in Scheme I to give the (R) free carboxylic acid.

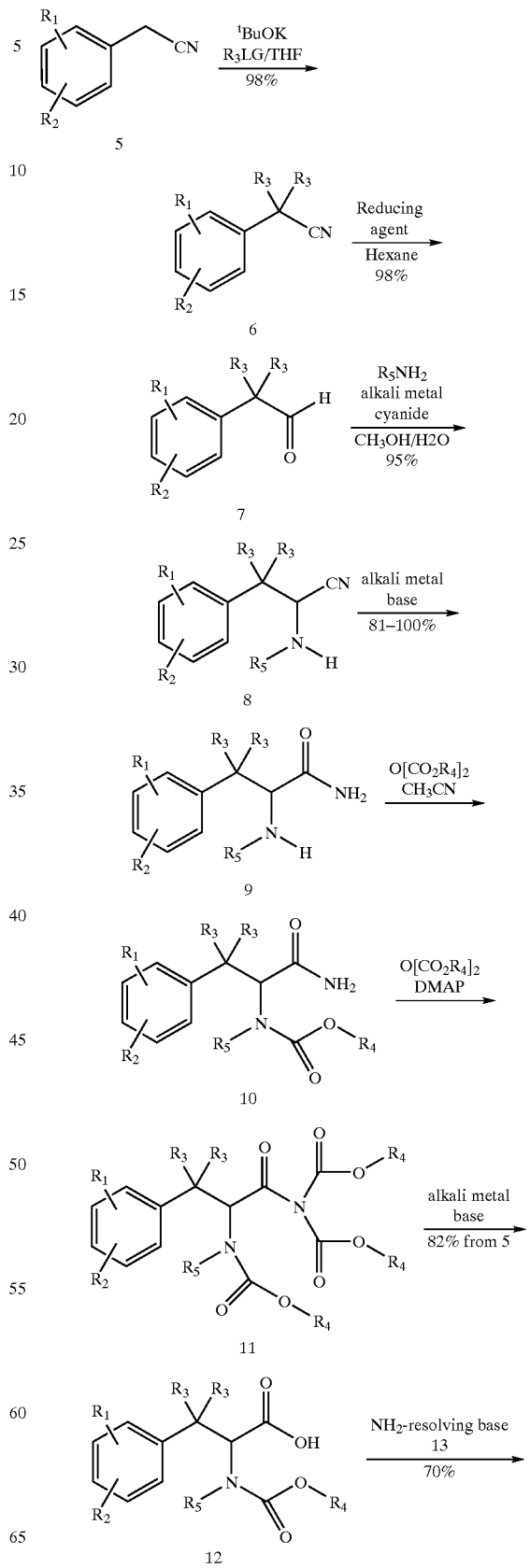

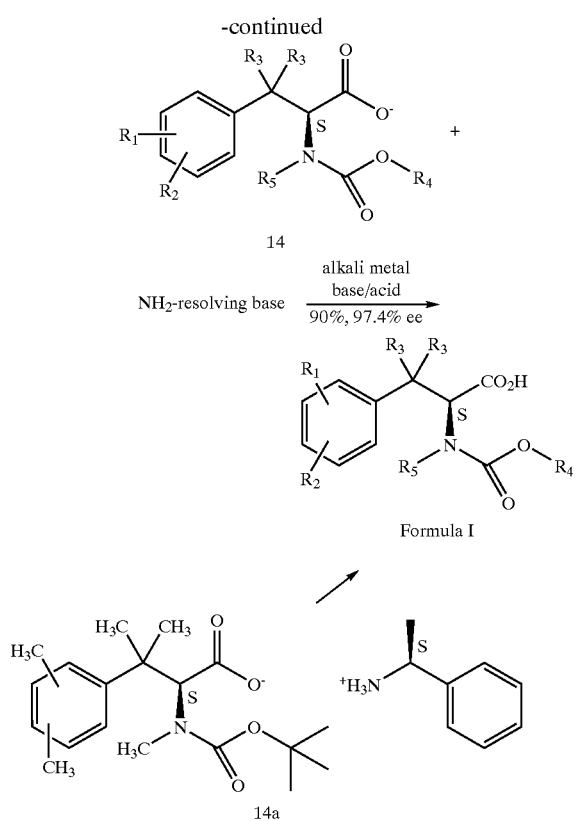

As described in Scheme II, compounds of Formula I are realized by an asymmetric Strecker approach using an enantiopure sulfinimine. Substituted benzaldehyde 15a where $R_1$ and $R_2$ are hereinbefore defined are converted to substituted oxirane 16 upon treatment with diphenylsulfonium isopropylide 15 using the low temperature conditions described (Corey, E. J. et al *Tetrahedron Lett.* 1967, 2325). The substituted oxirane 16 is selectively rearranged (>98% phenyl migration) to give aldehyde 7 upon treatment with a catalytic amount (5 mol %) of tris(pentafluorophenyl) borane $[(C_6F_5)_3B]$ in benzene (Yamamoto, H. et al *Synlett* 1995, 721) followed by subsequent treatment with (S)-(+)-p-toluenesulfinamide 17 and titanium ethoxide $[Ti(OEt)_4]$ to produce (S)-substituted-p-toluenesulfinamide 18 (Davis et al, *J. Org. Chem.* 1999, 64, 1403). Hydrocyanation of (S)-substituted-p-toluenesulfinamide 18 with the in situ prepared reagent derived from a dialkyl aluminum cyanide, preferably diethyl aluminum cyanide ($Et_2AlCN$) and isopropanol (IPA) affords a diastereomeric mixture of nitrile 19. In the case where aldehyde 7 is 2-methyl-2-phenylpropanal an 88:12 mixture of the diastereomeric $(S_S,2S)$—N-(p-toluenesulfinyl)-2-amino-3-methyl-3-phenylbutyronitrile and $(S_S,2R)$—N-(p-toluenesulfinyl)-2-amino-3-methyl-3-phenylbutyronitrile 19 (Davis, et al *J. Org. Chem.* 1996, 61, 440) is formed. Nitrogen alkylation (Semko, C. M. et al *J. Org. Chem.* 1993, 58, 696) of nitrile 19 with potassium hydroxide (KOH), tetrabutylammonium bromide(TBAB) and $R_5LG$ where $R_5$ is hereinbefore defined in a solvent such as THF to give substituted amine 20. Specifically, in the case where nitrile 19 is a mixture of $(S_S,2S)$—N-(p-toluenesulfinyl)-2-amino-3-methyl-3-phenylbutyronitrile and $(S_S,2R)$—N-(p-toluenesulfinyl)-2-amino-3-methyl-3-phenylbutyronitrile further reaction with an alkali metal hydroxide, preferably potassium hydroxide (KOH), tetrabutylammonium bromide(TBAB) and $R_5LG$ is preferably iodomethane ($CH_3I$) in THF generated the corresponding $(S_S,2S)$—N-(p-toluenesulfinamido-methyl)-3-methyl-3-phenylbutanenitrile 20 with the absence of observable epimerization at C-2. The $(S_S,2S)$—N-(p-toluenesulfinamido-methyl)-3-methyl-3-phenylbutanenitrile 20 could be readily separated via flash chromatography or crystallization. Further, deblocking substituted amine 20 to remove the p-toluenesulfinyl group is achieved in methanolic HCl to give amine 21. Reaction of amine 21 with an alkali metal hydroxide preferably lithium hydroxide optionally in the presence of an oxidizing agent such as hydrogen peroxide affords amide 22. Protection of the amine group of amide 22 is accomplished by reaction with an organic carbonate of the formula $O[CO_2R_4]_2$ where $R_4$ is hereinbefore defined in a solvent such as acetonitrile to afford blocked amine 23 optionally isolated. Protecting with the tert-butoxycarbonyl (Boc) group is preferred. Further reaction of blocked amine 23 with an organic carbonate of the formula $O[CO_2R_4]_2$ preferably di-tert-butyl dicarbonate in the presence of dimethylaminopyridine(DMAP) (at about 10% mol. percent) and optionally in the presence of an organic base which includes with diisopropylethylamine (DIEA) in a solvent such as acetonitrile gives triblocked amide 24. Hydrolysis of triblocked amide 24 with an alkali metal hydroxide preferably sodium hydroxide followed by acidifying with common acids which include hydrochloric and sulfuric, preferably with citric acid, to a pH 6 or less, preferably to a pH of 3–6, more preferably 4–6 and most preferably to 5–6 with citric acid afford compounds of Formula I.

Scheme II

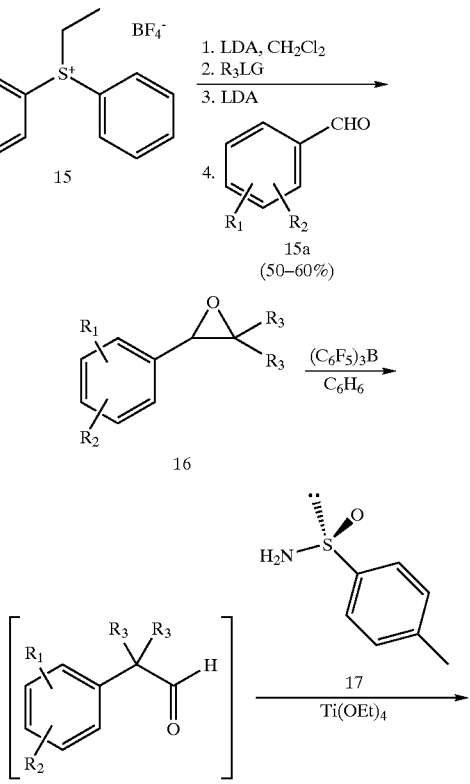

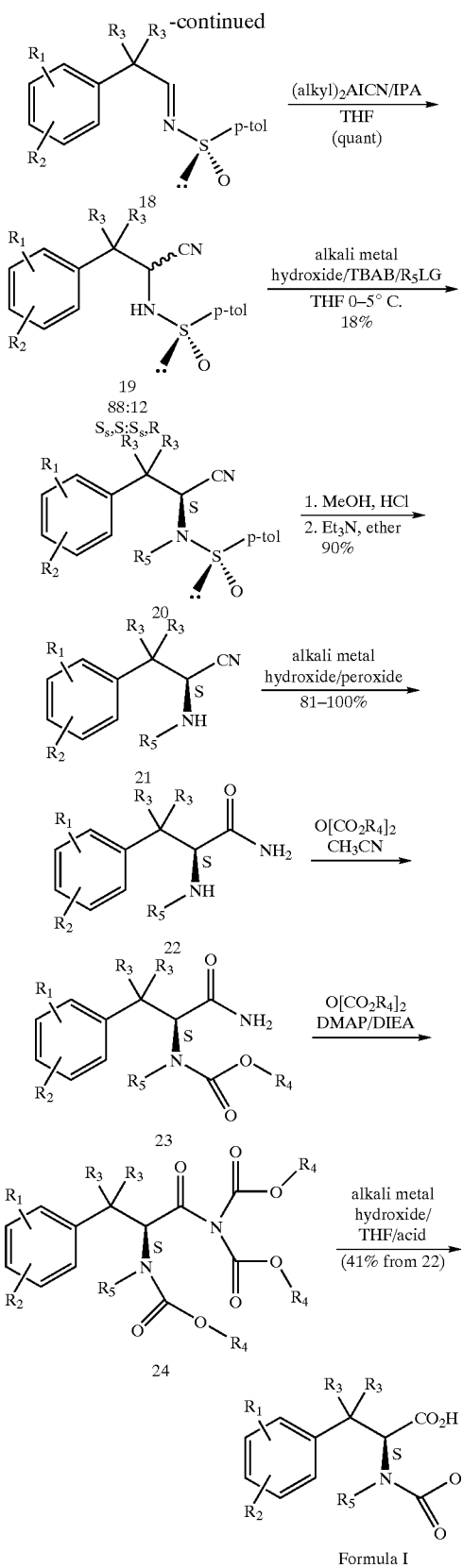

amine 26 in the presence of a coupling agent and an organic base affords ester 28 followed by alkaline metal hydroxide hydrolysis, preferably lithium hydroxide to obtain carboxylic acid 29.

Preferred coupling agents are selected from the group N,N'-dicyclohexylcarbodiimide plus 1-hydroxybenzotriazole, benzotriazol-1-yloxytris(dimethylamino)phosphonium hexafluorophosphate (BOP-reagent), N,N'bis[2-oxo-3-oxazolidinyl]phosphorodiamidic chloride (BOB Cl), diphenylphosphinyl chloride (DPP-Cl), diethoxyphosphoryl cyanide, 2-chloro-1-methylpyridinium iodide, phenyldichlorophosphate plus imidazole, 2-(1H-benzotriazole-1-yl)-1,1,3,3-tetramethyluronium tetrafluoroborate, 2-(1H-benzotriazole-1-yl)-1,1,3,3-tetramethyluronium hexafluorophosphate, bromo-tris-pyrrolidino-phosphonium hexafluorophosphate and benzotriazole-1-yl-oxy-tris-pyrrolidino-phosphonium hexafluorophosphate in the presence of N,N-diisopropylethylamine. A most preferred coupling agent is benzotriazole-1-yl-oxy-tris-pyrrolidino-phosphonium hexafluorophosphate 27 and organic base N,N-diisopropylethylamine in methylene chloride. Preferred organic bases include: N,N-diisopropylethylamine, N-methylmorpholine, N-methylpyrrolidine, triethylamine, 4-dimethylaminopyridine, 2,6-di-tert-butyl-4-methylpyridine and pyridine.

Scheme III

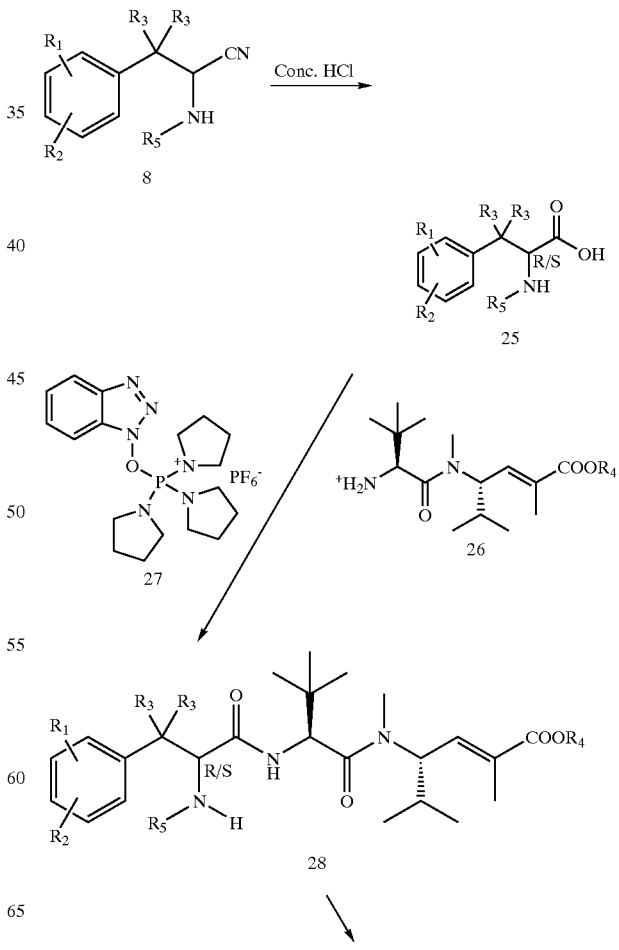

As outlined in Scheme III, carboxylic acid 25 is prepared by hydrolysis of nitrile 8 by refluxing in concentrated hydrochloric acid. Coupling of carboxylic acid 25 with

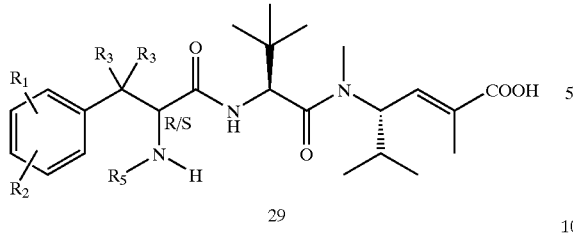

29

Further, as shown in Scheme IV, replacing carboxylic acid 25 with carboxylic acid 30 using the conditions described in Scheme III may be reacted with amine 26 to afford ester 31 which may be hydrolyzed with alkali metal hydroxide preferably lithium hydroxide to obtain carboxlic acid 32.

Scheme IV

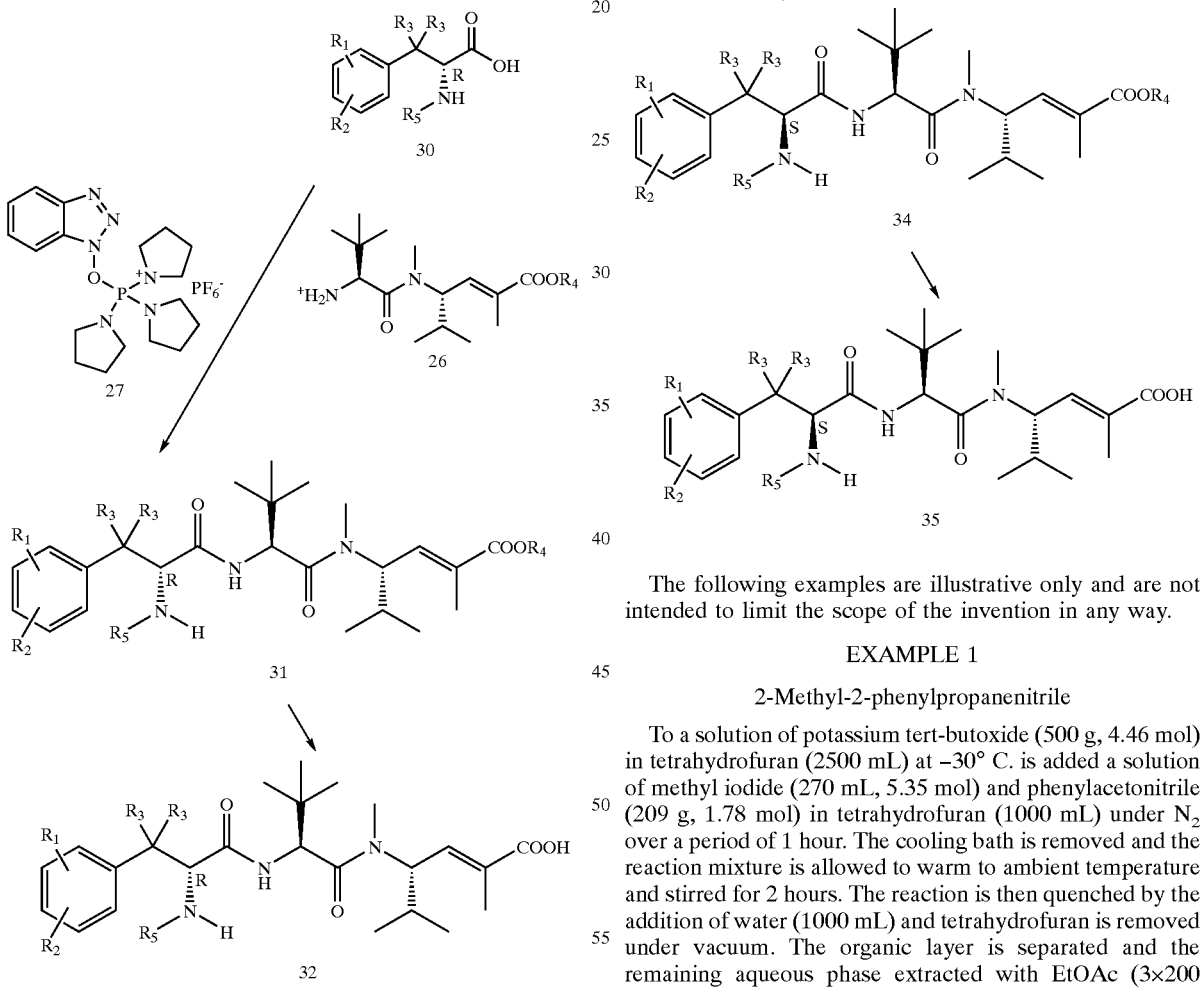

Further, as shown in Scheme V, replacing carboxylic acid 30 with carboxylic acid 33 using the conditions described in Scheme III may be reacted with amine 26 to afford ester 34 which may be hydrolyzed with alkali metal hydroxide preferably lithium hydroxide to obtain carboxylic acid 35. Carboxylic acid 33 may be prepared by acid hydrolysis of a compound of Formula I. A preferred acid is trifluoroacetic acid.

The following examples are illustrative only and are not intended to limit the scope of the invention in any way.

EXAMPLE 1

2-Methyl-2-phenylpropanenitrile

To a solution of potassium tert-butoxide (500 g, 4.46 mol) in tetrahydrofuran (2500 mL) at −30° C. is added a solution of methyl iodide (270 mL, 5.35 mol) and phenylacetonitrile (209 g, 1.78 mol) in tetrahydrofuran (1000 mL) under $N_2$ over a period of 1 hour. The cooling bath is removed and the reaction mixture is allowed to warm to ambient temperature and stirred for 2 hours. The reaction is then quenched by the addition of water (1000 mL) and tetrahydrofuran is removed under vacuum. The organic layer is separated and the remaining aqueous phase extracted with EtOAc (3×200 mL). The combined organic layers are washed with water (300 mL), brine (300 mL), and dried over $Na_2SO_4$. The organic extracts are filtered and concentrated under vacuum to give 2-methyl-2-phenylpropionitrile as an oil (253 g, 98% yield, 99.4% by HPLC area).

EXAMPLE 2

2-Methyl-2-phenylpropanal

To a solution of 2-methyl-2-phenylpropanenitrile (290 g, 2.00 mol) in hexane (2000 mL) at 0° C. under $N_2$ is added diisobutylaluminum hydride (DIBAL-H) (2600 mL, 1M in hexane) over a period of 80 minutes. The reaction mixture is stirred at 6–14° C. for 15 minutes, then allowed to warm to room temperature and stirred for 4 hours. The reaction mixture is cooled to 0° C. and $H_2O$ (50 mL) is added slowly during 1 hour. Aqueous HCl (900 mL, 15%) is then added slowly to maintain a gentle reflux. The reaction mixture is stirred for 17 hours and the organic phase is separated. The aqueous layer is extracted with ethyl acetate (400 mL) and the combined organic layers are washed with water (300 mL), brine (300 mL) and dried over $Na_2SO_4$. The organic extracts are filtered and concentrated to give 2-methyl-2-phenylpropanal as an oil (275 g, 92.8% yield, 98.2% by HPLC area).

EXAMPLE 3

3-Methyl-2-(methylamino)-3-phenylbutanenitrile

To a solution of potassium cyanide (103 g, 1.56 mol) and methylamine hydrochloride (106 g, 1.56 mol) in water (1000 mL) is added a solution of 2-methyl-2-phenylpropanal (222 g, 1.50 mol) in methanol (1000 mL) over a period of 30 minutes. An ice-water bath is used occasionally to maintain the reaction temperature between 20–25° C. The mixture is stirred at room temperature for 25 hours. Water (2000 mL) is then added and the reaction mixture is extracted with $CH_2Cl_2$ (3×800 mL). The combined organic extracts are washed with brine (500 mL) and dried over $Na_2SO_4$. The organic extracts are filtered and concentrated to give 3-methyl-2-(methylamino)-3-phenylbutanenitrile as an oil (274 g, 95% yield, 76.6% by HPLC area, NMR (>95%)). Evidence of decomposition on the HPLC/GC column is noted.

EXAMPLE 4

N,β,β-Trimethylphenylalaninamide

To a mixture of 3-methyl-2-(methylamino)-3-phenylbutanenitrile (78.0 g, 0.414 mol, 1 eq.) and lithium hydroxide (1N, 1660 mL, 4 eq.), cooled with ice-water bath to 16° C., is added $H_2O_2$ (30%, 171 mL, 4 eq.). The resulting reaction mixture is allowed to warm to ambient temperature and stirred for 24 hours. The reaction mixture is then cooled with ice-water bath to 10° C. and aqueous $Na_2SO_3$ (2.5N, 662 mL, 4 eq.) is added over a period of 10 minutes. The mixture is stirred for 3 hours, and then extracted with ethyl acetate (3×800 mL). The combined extracts are washed with brine and dried over $Na_2SO_4$. The organic extracts are filtered and concentrated to give the desired product as a white solid (69.8 g, 82%).

EXAMPLE 5

N-(tert-Butoxycarbonyl)-N,β,β-trimethylphenylalaninamide

To a solution of N,β,β-trimethylphenylalaninamide (2.0 g, 9.7 mmol) in acetonitrile (6.0 mL) at ambient temperature is added a solution of di-tert-butyl dicarbonate (2.33 g, 10.6 mmol) in acetonitrile (6.0 mL). After 24 hours, the reaction mixture is filtered and the product washed with acetonitrile (3 mL×2) to afford N-(tert-butoxycarbonyl)-N,β,β-trimethylphenylalaninamide (1.12 g, 40%, 97.6% HPLC area) as a white solid.

EXAMPLE 6

N,N,N-tris(tert-Butoxycarbonyl)-N,β,β-trimethylphenylalaninamide And

N-(tert-Butoxycarbonyl)-N,β,β-trimethylphenylalanine

To a solution of N,β,β-trimethylphenylalaninamide (83.0 g, 0.402 mol, 80% by HPLC area) in acetonitrile (500 mL) is added $Boc_2O$ (316 g, 1.45 mol). The resultant solution is stirred for 48 hours. N,N-dimethylaminopyridine (4.90 g, 0.0401 mol) and diisopropylethylamine (77.0 mL, 0.442 mol) are then added. After the mixture is stirred for 24 hours, water (1000 mL) is added. The mixture is extracted with heptane (3×500 mL) and the combined organic extracts are washed with water (3×500 mL) and brine (500 mL). The organic extracts are filtered and concentrated under vacuum to give N,N,N-tris(tert-butoxycarbonyl)-N,β,β-trimethylphenylalaninamide (202 g). Without further purification, N,N,N-tris(tert-butoxycarbonyl)-N,β,β-trimethylphenylalaninamide is dissolved in tetrahydrofuran (402 mL) and aqueous NaOH (5N, 402 mL) is added with vigorous stirring. After stirring for 4 hours, water (400 mL) is added. The solid is filtered off and washed with NaOH (0.5N, 3×200 mL). The mother liquor is concentrated under vacuum to remove the tetrahydrofuran. The resulting aqueous solution is extracted with heptane (3×500 mL) and acidified with citric acid to pH=5–6. The mixture is extracted with ethyl acetate (3×500 mL). The combined organic extracts are washed with brine and dried over $Na_2SO_4$. The organic extracts are filtered and concentrated to give N-(tert-butoxycarbonyl)-N,β,β-trimethylphenylalanine as an oil (81.0 g, 82% yield, 99.9% by HPLC area).

EXAMPLE 7

Salt of N-(tert-Butoxycarbonyl)-N,β,β-trimethyl-L-phenylalanine with (S)-(α)-methylbenzylamine (SAMBA)

To solution of N-(tert-butoxycarbonyl)-N,β,β-trimethylphenylalanine (47.4g, 0.154 mol) in dry ether (225 mL) is added (S)-(–)-α-methylbenzylamine (10.9 mL, 0.0849 mol) under $N_2$. The resultant solution is stirred for 15 minutes, then seeded with crystals of the salt of (S)-(–)-α-methylbenzylamine and N-(tert-butoxycarbonyl)-N,β,β-trimethylphenylalanine. After stirring for 22 hours, heptane (110 mL) is added. The mixture is then stirred at room temperature for 1 hour and cooled to 0° C. and stirred for an additional hour. The precipitate is filtered and washed with heptane (3×50 mL) and dried under vacuum to give the desired product as a white solid (23.0 g, 70%, 97.5% ee).

Using the conditions of Example 7 the following compounds are prepared:

| RESOLVING BASE | R/S- EPIMER | HPLC (%) | OVERALL YIELD (%) |
|---|---|---|---|
| SAMBA | 2.7/97.3 | 97.8 | 42 |
| SAMBA | 1.3/97.6 | 96.3 | 62 |
| (1R,2R)-(–)pseudoephedrin | Not crystalline | | |
| (1S,2R)-(+)-methylephedrin | Not crystalline | | |
| (1R,2S)-(–)-norephedrin | 2.7/97.3 | 98.3 | 56 |
| (1S,2R)-(+)-norephedrin | 95.7/4.3 | 96.6 | 100 |
| R-(+)-α-methyl-4-nitro-benzylamine | Not crystalline | | |
| S-(–)-α-methyl-4-nitro-benzylamine | 2.9/97.1 | 99.5 | 74 |
| RAMBA | 99.4/0.6 | 99.3 | 78 |

EXAMPLE 8

N-(tert-Butoxycarbonyl)-N,β,β-trimethyl-L-phenylalanine

The salt of N-(tert-butoxycarbonyl)-N,β,β-trimethyl-L-phenylalanine with (S)-(–)-α-methylbenzylamine (SAMBA) (37.9 g, 88.5 mmol) is dissolved in 0.5N NaOH (265 mL, 133 mmol). The resultant solution is stirred for 10 minutes. The clear solution is extracted with heptane (4×200 mL) and neutralized with citric acid to pH=5–6. The resultant cloudy solution is extracted with ethyl acetate (3×300 mL) and dried over $Na_2SO_4$. The organic extracts are filtered and concentrated under vacuum to give N-(tert-butoxycarbonyl)-N,β,β-trimethyl-L-phenylalanine as white solid (24.5 g, 90% yield, 99.6% by HPLC area, 97.4% ee).

EXAMPLE 9

(S)—N-(2-Methyl-2-phenylpropylidene)-p-toluenesulfinamide

To a stirred solution of 2.5 g of 2,2-dimethyl-3-phenyloxirane (16 mmol) in 85 mL of anhydrous benzene is added 0.415 g (0.362 mmol, 5 mol %) of tris (pentafluorophenyl) borane. The light yellow solution is stirred at 25° C. for 19 hours. The reaction mixture containing the 2-methyl-2-phenylpropanal is then treated with (S)-p-toluenesulfinamide (2.3 g, 15 mmol) followed by a solution of 16 mL (73 mmol) titanium ethoxide in 155 mL of benzene. The yellow solution is stirred at 25° C. for 24 hours then cooled to 5–10° C. and quenched with 245 mL of water. The mixture is filtered through diatomaceous earth, and the filter cake washed with methylene chloride (4×50 mL). The aqueous layer is washed with methylene chloride (1×25 mL). The combined organic layers are dried ($MgSO_4$) and concentrated under reduced pressure to give 3.74 g (81%) of the desired product as a white solid. The product is used without further purification in the next step.

EXAMPLE 10

($S_S$,2S)—N-(p-Toluenesulfinyl)-2-amino-3-methyl-3-phenylbutyronitrile and ($S_S$,2R)—N-(p-Toluenesulfinyl)-2-amino-3-methyl-3-phenylbutyronitrile To a stirred, ice-cold solution of 6.8 mL of a 1M solution of diethyl aluminum cyanide in toluene (Aldrich, 6.8 mmol) in 70 mL of tetrahydrofuran is added 0.94 mL (12.3 mmol) of 2-propanol dropwise. After 10 minutes, this solution is added dropwise to a solution of (S)—N-(2-methyl-2-phenylpropylidene)-p-toluenesulfinamide (3.4 g, 11.7 mmol) in 70 mL of THF pre-cooled to −78° C. The reaction mixture is kept at −78° C. for 20 minutes., then warmed to 25° C. and stirred for 1 hour. The reaction mixture is recooled to −78° C. and quenched with saturated ammonium chloride (86 mL). The resulting mixture is diluted with ethyl acetate (120 mL) and filtered through diatomaceous earth. The filter cake is washed with ethyl acetate (40 mL), and the organic layer is dried ($MgSO_4$) and concentrated under reduced pressure to give the desired product as a tan oil (3.9 g, 105%) which is used without further purification in the next step. Analysis by $^1$H NMR revealed an 88:12 ratio of $S_S,S:S_S,R$ diastereomers.

EXAMPLE 11

($S_S$,2S)—N-(p-Toluenesulfinamido-methyl)-3-methyl-3-phenylbutanenitrile

To an ice-cold, stirred suspension of 0.12 g of KOH (85%, 0.10 g, 1.8 mmol), 0.11 g (0.35 mmol) of tetrabutylammonium bromide and THF (8 mL) is added a solution of 0.5 g (1.6 mmol) ($S_S$,2S)—N-(p-toluenesulfinyl)-2-amino-3-methyl-3-phenylbutyronitrile and $S_S$,2R)—N-(p-toluenesulfinyl)-2-amino-3-methyl-3-phenylbutyronitrile and methyl iodide (0.50 mL, 8.0 mmol) in THF (4 mL). The reaction mixture is kept at 0–5° C. for 50 minutes, then transferred to a separatory funnel containing diethyl ether (80 mL) and water (8 mL). The organic layer is washed with water (2×8 mL) and brine (1×4 mL), dried ($MgSO_4$), and concentrated under reduced pressure to give 0.45 g of a yellow oil. The crude product is purified by flash chromatography (FlashElute™ 40M cartridge, 78:22 hexane:ethyl acetate, 60×8 mL fractions) to give 91 mg (18%) of the desired product as a white solid (>95% de by $^1$H NMR). Recrystallization from methylene chloride/hexanes afforded the desired product as long transparent rods which are judged to be >99% pure diastereomer by $^1$H NMR. The stereochemical assignments are verified by x-ray crystallography.

EXAMPLE 12

(2S)-3-Methyl-2-(methylamino)-3-phenylbutanenitrile

The ($S_S$,2S)—N-(p-toluenesulfinamido-methyl)-3-methyl-3-phenylbutanenitrile (0.956 g, 2.89 mmol) is added to 1 N HCl in methanol (generated via the addition of 13.6 mL of acetyl chloride to 195 mL of methanol). The reaction mixture is allowed to stand overnight then concentrated to give 1.06 g of white solid. The solid is slurried with 40 mL of ether for 20 minutes, filtered, and washed with ether (80 mL). The yield of the hydrochloride salt is 638 mg (97%). The salt is suspended in ether (30 mL) and 0.4 mL (2.9 mmol) of triethylamine is added. The mixture is stirred for 20 minutes and filtered. The filtrate is concentrated under reduced pressure to give 0.48 g (90%) of the desired product as a colorless oil.

EXAMPLE 13

N,β,β-Trimethyl-L-phenylalaninamide,

N,N,N-tris(tert-Butoxycarbonyl)-N,β,β-trimethyl-L-phenylalaninamide, and

N-(tert-Butoxycarbonyl)-N,β,β-trimethyl-L-phenylalanine

To a stirred suspension of (2S)-3-methyl-2-(methylamino)-3-phenylbutanenitrile (0.48 g, 2.5 mmol) in 10 mL of 1 N lithium hydroxide is added 1.0 mL of 30% $H_2O_2$. The reaction mixture is stirred vigorously at 25° C. for 40 h, then quenched with 4 mL of 2.5 N $Na_2SO_3$. The resulting mixture is stirred for 3 hours and extracted with ethyl acetate. The organic layer is dried ($Na_2SO_4$) and concentrated under reduced pressure to give 0.47 g (89%) of N,β,β-trimethyl-L-phenylalaninamide as a colorless solid.

To a stirred solution of N,β,β-trimethyl-L-phenylalaninamide (0.47 g, 2.24 mmol) in 2.8 mL of acetonitrile is added 1.75 g (8.00 mmol) $Boc_2O$. The reaction mixture is stirred for 48 hours then 27 mg (0.22 mmol) of dimethylaminopyridine and 0.43 mL (2.5 mmol) of N,N-diisopropylethylamine are added. After 24 hours, 6 mL of water is added, and the reaction mixture is washed with heptane (3×3mL). The organic layer is washed with water (3×3 mL) and brine (1×3mL) and concentrated under reduced pressure to give 1.13 g of N,N,N-tris(tert-butoxycarbonyl)-N,β,β-trimethyl-L-phenylalaninamide as a thick oil. The oil, N,N,N-tris(tert-butoxycarbonyl)-N,β,β-trimethyl-L-phenylalaninamide is taken up into tetrahydrofuran (2 mL) and treated with 5N NaOH (2 mL). The reaction mixture is stirred for 4 hours then water (4 mL) is added. The reaction mixture is filtered, washed with heptane (3×3mL), and acidified with citric acid. N-(tert-butoxycarbonyl)-N,β,β-trimethyl-L-phenylalanine (0.33 g, 41%) is obtained by extraction with ethyl acetate followed by concentration.

EXAMPLE 14

N,β,β-Trimethylphenylalanine

A mixture of 3-methyl-2-(methylamino)-3-phenylbutanenitrile (3.31 g, 4.85 mmol) and Conc. HCl (12 M, 100 mL) was heated to reflux for 65 hours. The mixture is extracted with ethyl acetate and the aqueous phase is evaporated to dryness. The residue is dissolved into 1 N NaOH (30 mL) and washed with ethyl acetate again. The aqueous phase is neutralized with conc. HCl to pH=4–5, then evaporated to dryness. The solid is washed with water and dried to give the desired product as a white solid (2.2 g, 66%, 96.4% HPLC area).

EXAMPLE 15

N,β,β-Trimethylphenylalanyl-N¹-[(1S,2E)-3-carboethoxy-1-isopropylbut-2-enyl]-N¹,3-dimethyl-L-valinamide N,β,β-trimethylphenylalanine (0.511 g, 2.47 mmol) is suspended in methylene chloride (7 mL) followed by addition of N,N-diisopropylethylamine (0.87 mL; 5.00 mmol) and a solution of ethyl (2E,4S)-2,5-dimethyl-4-[methyl(3-methyl-L-valyl)amino]hex-2-enoate (2.63 mmol) in methylene chloride (3 mL). The mixture is cooled to 3.5° C. and the coupling reagent (benzotriazole-1-yl-oxy-tris-pyrrolidino-phosphonium hexafluorophosphate; 1.24 g; 2.39 mmol) is added portionwise. The reaction mixture is stirred overnight under nitrogen. An HPLC showed a 1:1 mixture of the SSS and RSS epimers of N,β,β-trimethylphenylalanyl-N¹-[(1S,2E)-3-carboethoxy-1-isopropylbut-2-enyl]-N¹,3-dimethyl-L-valinamide accompanied by a small amount of N,β,β-trimethylphenylalanine and traces of ethyl (2E,4S)-2, 5-dimethyl-4-[methyl(3-methyl-L-valyl)amino]hex-2-enoate. Heptane (10 mL) is added and the suspension is filtered. The filtrate is evaporated to an oil and treated with more heptane. The heptane treatment—decantation is repeated four times. All the heptane extracts are combined and evaporated, dissolved in 3:1 hexane-ethyl acetate, and passed through a short silica gel pad. Evaporation of the solution gave an oil (1.02 g, 82% yield, 95.1% High Pressure Liquid Chromatography (HPLC) area, Retention Time (RT) identical with the reference samples of the product epimers).

EXAMPLE 16

N,β,β-Trimethylphenylalanyl-N¹-[(1S,2E)-3-carboxy-1-isopropylbut-2-enyl]-N¹, 3-dimethyl-L-valinamide N,β,β-trimethylphenylalanyl-N¹-[(1S,2E)-3-carboethoxy-1-isopropylbut-2-enyl]-N¹, 3-dimethyl-L-valinamide (Example 15) is hydrolyzed in the presence of base to obtain the product of the example.

EXAMPLE 17

N,β,β-Trimethyl-L-phenylalanyl-N¹-[(1S,2E)-3-carboethoxy-1-isopropyl-but-2-enyl-N,β,β-dimethyl-L-valinamide Using the conditions of Example 15 and N,β,β-trimethyl-L-phenylalanine the product of the Example may be obtained.

EXAMPLE 18

N,β,β-trimethyl-L-phenylalanyl-N¹-[(1S,2E)-3-carboxy-1-isopropylbut-2-enyl]-N¹, 3-dimethyl-L-valinamide Using the conditions of Example 16, and the product of Example 17, the product of the Example may be obtained.

We claim:

1. A process for the preparation of a compound of Formula I:

Formula I

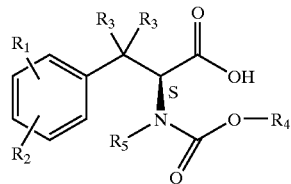

wherein:

$R_1$ and $R_2$ are independently selected from H, straight chain alkyl of 1 to 4 carbon atoms, halogen and alkoxy of 1 to 4 carbon atoms;

$R_3$ is straight chain alkyl of 1 to 4 carbon atoms;

$R_4$ is straight chain alkyl of 1 to 4 carbon atoms and branched chain alkyl of 3 to 4 carbon atoms;

$R_5$ is straight chain alkyl of 1 to 4 carbon atoms;

comprising:

a) treating a nitrile of the formula:

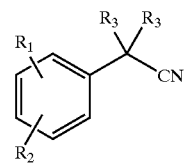

with a reducing agent followed by acid hydrolysis to obtain an aldehyde of the formula:

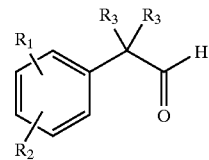

b) reacting the aldehyde (step a) with alkali metal cyanide in the presence of an alkyl amine of the formula $R_5NH_2$ to obtain nitrile of the formula:

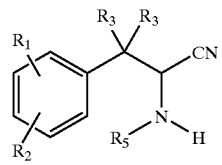

c) hydrolyzing the nitrile (step b) with an alkali metal hydroxide to give an amide of the formula:

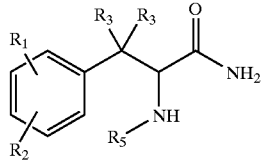

d) reacting the amide (step c) with an organic carbonate, of the formula O[CO$_2$R$_4$]$_2$ wherein each R$_4$ is taken independently in the presence of dimethylaminopyridine (DMAP) to obtain a triblocked amide of the formula:

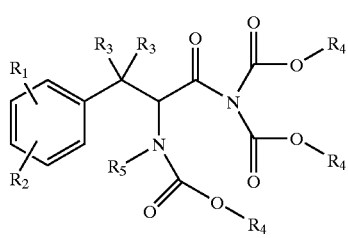

e) hydrolyzing triblocked amide (step d) with an alkali metal hydroxide to give racemic blocked amine of the formula:

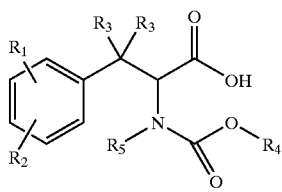

f) reacting racemic blocked amine (step e) with a resolving base (NH$_2$-resolving base) to obtain a resolved blocked amine salt of the formula:

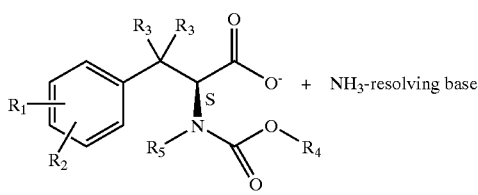

and g) treating the resolved blocked amine salt with aqueous alkali metal hydroxide and acidifying with acid to give a compound of Formula I:

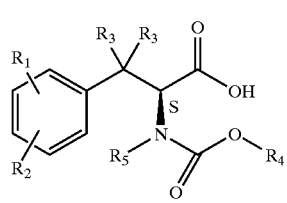

2. The process according to claim 1, wherein the reducing agent in step a is tin chloride/hydrochloric acid, lithium aluminum hydride, or diisobutylaluminum hydride (DIBAL-H).

3. The process according to claim 2, wherein the reducing agent is diisobutylaluminum hydride (DIBAL-H).

4. The process according to claim 1, wherein the alkali metal cyanide in step b is sodium cyanide, potassium cyanide or lithium cyanide.

5. The process according to claim 4, wherein the alkali metal cyanide is potassium cyanide.

6. The process according to claim 1, wherein the alkylamine is methylamine.

7. The process according to claim 1, wherein the alkali metal hydroxide in step c is sodium hydroxide, potassium hydroxide or lithium hydroxide.

8. The process according to claim 7, wherein the alkali metal hydroxide is lithium hydroxide.

9. The process according to claim 7, optionally including the oxidizing agent hydrogen peroxide in step c.

10. The process according to claim 1, wherein the organic carbonate in step d is t-butyl dicarbonate.

11. The process according to claim 1, step d, optionally including the organic base N,N-diisopropylethylamine in step d.

12. The process according to claim 1 wherein the alkali metal hydroxide in step e is sodium hydroxide, potassium hydroxide or lithium hydroxide.

13. The process according to claim 12, wherein the alkali metal hydroxide is sodium hydroxide.

14. The process according to claim 1 wherein the resolving base in step f is (S)-(–)-α-methylbenzylamine, (S)-(–)-α-methyl-4-nitro-benzylamine, (1R,2S)-(–)-norephedrin, or (1S,2R)-(+)-norephedrin.

15. The process according to claim 14, wherein the resolving base is (S)-(α)-methylbenzylamine or (S)-(–)-methyl-4-nitro-benzylamine.

16. The process according to claim 15, wherein the resolving base is (S)-(–)-α-methylbenzylamine.

17. The process according to claim 1, wherein the alkali metal hydroxide in step g is sodium hydroxide, potassium hydroxide, lithium hydroxide or sodium carbonate.

18. The process according to claim 17, wherein the alkali metal hydroxide is sodium hydroxide.

19. The process according to claim 1, wherein the acids hydrochloric, sulfuric or citric acid in step g adjust the pH to 6 or less.

20. The process according to claim 19, wherein the pH is adjusted to 3 to 6.

21. The process according to claim 20, wherein the pH is adjusted to 4 to 6.

22. The process according to claim 21 wherein the pH is adjusted to 5 to 6 with citric acid.

23. A process for the preparation of a compound of the formula:

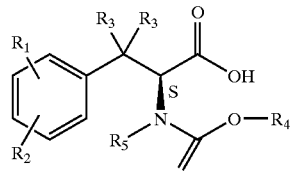

wherein:
R$_1$ and R$_2$ are independently selected from H, straight chain alkyl of 1 to 4 carbon atoms, halogen and alkoxy of 1 to 4 carbon atoms;
R$_3$ is straight chain alkyl of 1 to 4 carbon atoms;
R$_4$ is straight chain alkyl of 1 to 4 carbon atoms and branched chain alkyl of 3 to 4 carbon atoms;
R$_5$ is straight chain alkyl of 1 to 4 carbon atoms;

comprising:

a) reacting a racemic blocked amine of the formula:

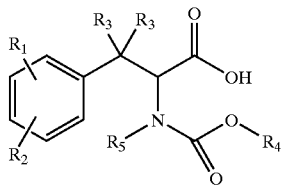

with a resolving base (NH$_2$-resolving base) to obtain a resolved blocked amine salt of the formula:

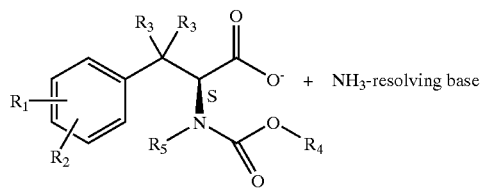

and b) treating the resolved blocked amine salt with aqueous alkali metal hydroxide and acidifying with acid to give a compound of Formula I

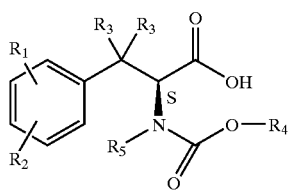

Formula I

24. The process according to claim 23 wherein the resolving base in step a is (S)-(−)-α-methylbenzylamine, (S)-(−)-α-methyl-4-nitro-benzylamine, (1R,2S)-(−)-norephedrin, or (1S,2R)-(+)-norephedrin.

25. The process according to claim 24, wherein the resolving base is (S)-(−)-α-methylbenzylamine or (S)-(−)-α-methyl-4-nitro-benzylamine.

26. The process according to claim 25, wherein the resolving base is (S)-(−)-α-methylbenzylamine.

27. The process according to claim 23, wherein the alkali metal hydroxide in step b is sodium hydroxide, potassium hydroxide, lithium hydroxide or sodium carbonate.

28. The process according to claim 27, wherein the alkali metal hydroxide is sodium hydroxide.

29. The process according to claim 23, wherein the acids hydrochloric, sulfuric or citric acid in step h adjust the pH to 6 or less.

30. The process according to claim 29, wherein the pH is adjusted to 3 to 6.

31. The process according to claim 30, wherein the pH is adjusted to 4 to 6.

32. The process according to claim 31 wherein the pH is adjusted to 5 to 6 with citric acid.

33. A process for the preparation of a compound of Formula I:

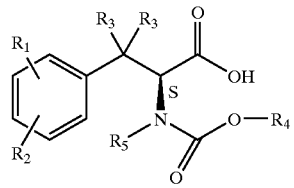

Formula I wherein:

R$_1$ and R$_2$ are independently selected from H, straight chain alkyl of 1 to 4 carbon atoms, halogen and alkoxy of 1 to 4 carbon atoms;

R$_3$ is straight chain alkyl of 1 to 4 carbon atoms;

R$_4$ is straight chain alkyl of 1 to 4 carbon atoms and branched chain alkyl of 3 to 4 carbon atoms;

R$_5$ is straight chain alkyl of 1 to 4 carbon atoms;

comprising:

a) deblocking substituted amine of the formula:

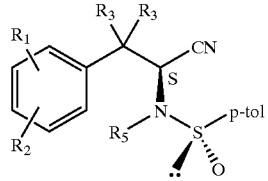

with acid to give nitrile of the formula:

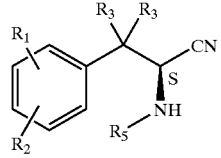

b) hydrolyzing the nitrile (step a) in the presence of an alkali metal hydroxide to obtain an amide of the formula:

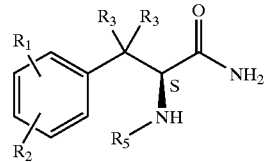

c) reacting the amide (step b) with an organic carbonate of the formula O[CO$_2$R$_4$]$_2$ wherein R$_4$ is taken independently in the presence of dimethylaminopyridine (DMAP) to give triblocked amide of the formula:

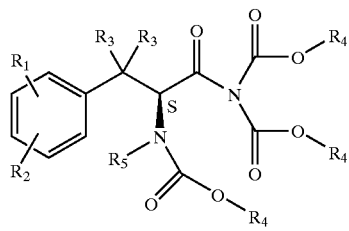

and;

d) hydrolyzing triblocked amide (step c) with an alkali metal hydroxide and acidifying with acid to obtain a compound of Formula I:

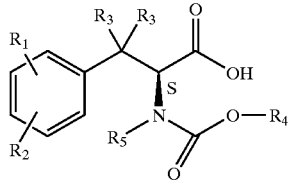

Formula I

34. The process according to claim 33 step a wherein the acid is methanolic HCl.

35. The process according to claim 33 step b wherein the alkali metal hydroxide in step b is sodium hydroxide, potassium hydroxide or lithium hydroxide.

36. The process according to claim 35 wherein the alkali metal hydroxide is lithium hydroxide.

37. The process according to claim 36 including an optionally added oxidizing agent which is hydrogen peroxide.

38. The process according to claim 33, wherein the organic carbonate in step c is t-butyl dicarbonate.

39. The process according to claim 38 optionally including an organic base in step c which is N,N-diisopropylethylamine.

40. The process according to claim 33 wherein the alkali metal hydroxide in step d is sodium hydroxide, potassium hydroxide or lithium hydroxide.

41. The process according to claim 40, wherein the alkali metal hydroxide is sodium hydroxide.

42. The process according to claim 33, step d wherein the acids hydrochloric, sulfuric or citric acid in step d adjust the pH to 6 or less.

43. The process according to claim 42, wherein the pH is adjusted to 3 to 6.

44. The process according to claim 43, wherein the pH is adjusted to 4 to 6.

45. The process according to claim 44 wherein the pH is adjusted to 5 to 6 with citric acid.

* * * * *